United States Patent [19]

Rygiel

[11] 4,397,643
[45] Aug. 9, 1983

[54] DRAINAGE COLLECTION DEVICE WITH DISPOSABLE LINER

[75] Inventor: Sharon A. Rygiel, Miami, Fla.

[73] Assignee: Sherwood Medical Company, St. Louis, Mo.

[21] Appl. No.: 259,886

[22] Filed: May 4, 1981

[51] Int. Cl.³ .............................................. A61M 1/00
[52] U.S. Cl. .................................. 604/317; 128/760; 215/11 E
[58] Field of Search ............... 128/909, 275, 276, 277, 128/278, 760, 765; 215/11 E; 220/403, 404, 470, 85 B; 141/8, 10, 67, 59; 222/209, 214, 387, 105, 386.5, 131; 137/205; 604/317

[56] References Cited

U.S. PATENT DOCUMENTS

| | | | |
|---|---|---|---|
| 2,397,257 | 3/1946 | Goland et al. | 128/276 |
| 2,970,042 | 1/1961 | Lagerwey | 220/403 |
| 3,163,544 | 12/1964 | Valyi | 220/404 |
| 3,680,560 | 8/1972 | Pannier, Jr. et al. | 128/276 |
| 3,719,197 | 3/1973 | Pannier, Jr. et al. | 137/205 |
| 3,784,039 | 1/1974 | Marco | 222/105 |
| 3,814,098 | 6/1974 | Deaton | 128/276 |
| 4,098,434 | 7/1978 | Uhlig | 222/105 |
| 4,306,557 | 12/1981 | North | 128/276 |

FOREIGN PATENT DOCUMENTS 963339 2/1975 Canada ............................... 128/276

OTHER PUBLICATIONS

Catalog Cut, Medi-Vac Corporation, Abilene, Texas, "CRD System", 1980.

Primary Examiner—Richard J. Apley
Assistant Examiner—J. L. Kruter
Attorney, Agent, or Firm—Stanley N. Garber; William R. O'Meara

[57] ABSTRACT

A drainage collection device is provided which includes a relatively rigid reusable canister and a collapsible drainage collection liner. The lid and upper wall of the liner have cooperating connectors for holding the upper end of the liner in place. The canister has an abutment adjacent the lower end for holding the lower end portion of the liner adjacent the lower end of the canister. The liner has a bellows-like sidewall so that the liner can be stored in a collapsed condition.

19 Claims, 6 Drawing Figures

U.S. Patent Aug. 9, 1983 4,397,643
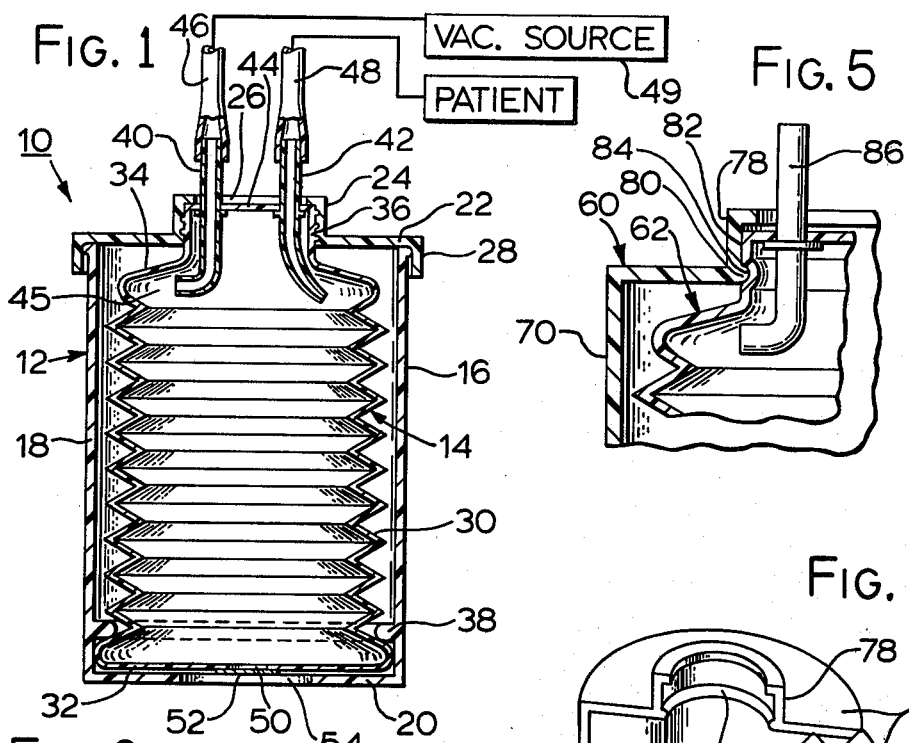
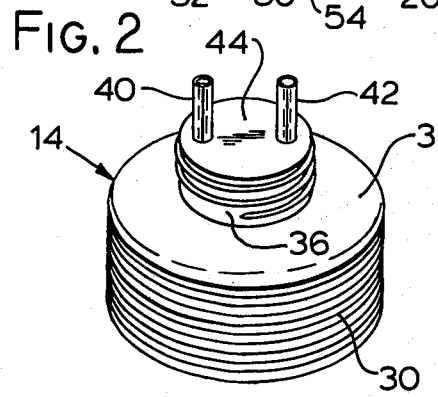
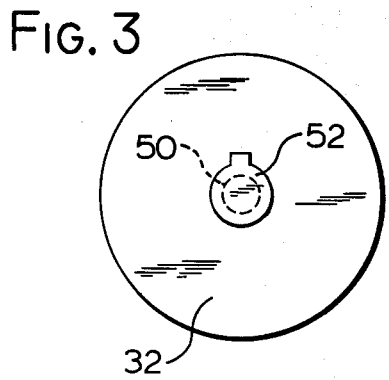
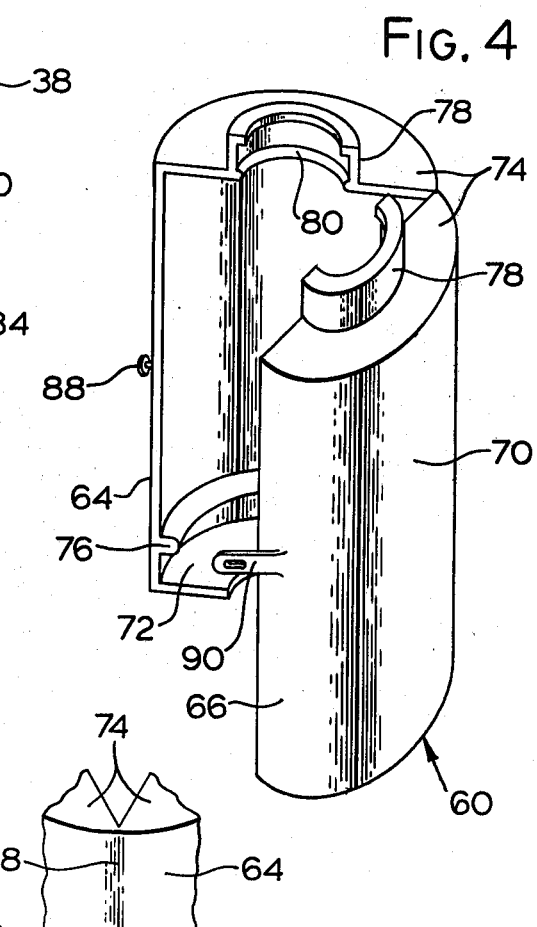

DRAINAGE COLLECTION DEVICE WITH DISPOSABLE LINER

DESCRIPTION

1. Technical Field

This invention relates to body fluid drainage collection devices and more particularly to such devices that are connectable to suction sources and which have disposable liners.

2. Background Art

Body fluid collection devices generally include a collection container having a body fluid inlet port connectable to a patient, such as to a body wound, and a suction port connectable to a source of vacuum for facilitating the flow of body fluid drainage into the container.

Some drainage collection devices utilize a disposable rigid plastic canister with the drainage inlet and suction ports provided in the canister lid. Such devices are relatively expensive because of the relatively large amount of plastic material required. Also, considerable storage space is required to store disposable or single-use rigid collection devices.

In order to reduce costs and storage space, drainage collection devices of the type having a reusable rigid canister and inexpensive disposable liners of pliable plastic have been employed. The disposable liners may be made of thin plastic so that they are inexpensive and can be stored in the collapsed or uninflated condition thereby requiring less storage space. However, some such devices have required relatively complicated and expensive arrangements for securing the liner in the canister and maintaining them in the expanded condition when suction is applied to the interior of the liner. For example, in U.S. Pat. No. 3,719,197, a second suction port connected to the suction line is used to provide a vacuum inside the canister but outside the liner to countervail the vacuum inside the liner and thereby prevent the liner from collapsing.

In one construction shown in U.S. Pat. No. 3,680,560, a passage with a filter is provided through the wall of the liner within the canister so that gas or air flows from inside the liner to the interior of the canister with the pressure differential due to the filter maintaining the liner expanded.

In U.S. Pat. No. 2,397,257, a collapsible bellow-like chamber is supported by telescopic struts and wing nuts. The chamber has a gasket to make it airtight. This arrangement is complicated to use and is relatively expensive.

DISCLOSURE OF THE INVENTION

An object of the present invention is to provide a relatively economical drainage collection device which has a disposable liner, can be stored in a collapsed condition, and wherein the device overcomes one or more of the above problems associated with drainage devices employing liners.

In accordance with one aspect of the present invention, a drainage collection device is provided which includes a relatively rigid canister, and a flexible, collapsible liner for insertion into the canister. The canister and liner have a releasable connection at the upper end for holding the upper end portion of the liner in place, and a holding member adjacent the lower end of the canister is used to hold the lower end portion of the liner so as to maintain the liner in an expanded condition.

These, as well as other objects and advantages of the present invention, will become apparent from the following detailed description and accompanying drawing.

BRIEF DESCRIPTION OF THE DRAWING

FIG. 1 is an elevational cross-sectional view of a drainage collection device in accordance with a preferred embodiment of the present invention;

FIG. 2 is a perspective view of the liner of FIG. 1 but in a collapsed condition;

FIG. 3 is a plan view of the bottom of the liner of FIG. 1;

FIG. 4 is a perspective view of a canister in accordance with a modified embodiment of the invention and shown in an open condition;

FIG. 5 is a fragmentary, elevational cross-sectional view on an enlarged scale of the canister of FIG. 4 with a liner inside; and FIG. 6 is a fragmentary perspective view showing a portion of the canister of FIG. 4.

DETAILED DESCRIPTION OF THE INVENTION

Referring now to the drawings and more particularly to FIG. 1, a body fluid drainage collection device 10 is shown including a reusable canister 12, and a disposable collapsible fluid collection receptacle or liner 14 connected within the canister 12 in an expanded condition.

The canister 12 includes a container 16 having a generally cylindrical sidewall 18 and a bottom wall 20 integral with the sidewall 18. Canister 12 also includes an upper wall or lid 22 having a central internally threaded collar 24 for securing the liner 14 in place, as will be further discussed, and a central opening 26. The lid has a generally cylindrical depending flange 28 forming an internal annular shoulder. The flange 28 frictionally receives the upper end of the container 16 and secures the lid 22 to the container. The lid 22 can be forced or snapped over the upper end of the container sidewall and can be removed when desired by forcing it upwardly and off of the container. The container 16 and lid 22 may be formed of a suitable plastic with walls sufficiently thick to make the canister 12 substantially rigid. For example, the canister 12 may be made of polystyrene, polycarbonate or polypropylene, and preferably of clear plastic for viewing the drainage material.

The drainage collection liner 14, shown also in FIGS. 2 and 3, is of accordion or bellow construction and has a pleated, generally cylindrical, sidewall 30, a bottom wall 32, and an upper wall 34 having an externally threaded neck 36. Neck 36 is shown in FIG. 1 threaded into the threaded collar 24 of the canister lid 22 to hold the upper end portion of the liner 14 in place. The lower end portion of the liner is held in place at the bottom of the canister 12 by an annular holding abutment or ring 38 integrally formed on the interior of the container sidewall 18. The ring 38 is shown extending over the bottom wall 32 and engaging a lower portion of the liner 14 to secure the bottom wall at the lower end of the canister 12 and maintain the liner in its expanded condition, as shown in FIG. 1.

In FIG. 2, the liner 14 is shown in its deflated or collapsed condition. The liner can be packaged, shipped, and stored relatively economically in the collapsed condition since the volume of space it occupies in such condition is substantially less than when it is in its expanded condition.

The liner 14 also includes a suction or gas outlet port shown as a conduit or tube connector 40, and a body drainage inlet port shown as a conduit or tube connector 42. The inlet and outlet ports 40 and 42 are connected to a central top wall portion 44 of the neck 36 of the upper wall 34. The ports 40 and 42 are in fluid communication with the collection chamber, indicated at 45, and are shown connected respectively to a suction tube 46 and a drainage tube 48. The tube 46 may be connected to a source of vacuum 49 such as a conventional suction source generally found in hospital rooms. A conventional or suitable overflow valve (not shown) may be connected in series with the tube connector 40 or tube 46. Also, a filter (not shown) may also be used in series with the tube connector 40 or tube 46 to prevent matter and bacteria from flowing into the hospital suction system.

The tube 48 may be catheter or be connected to a catheter, for example, one that is inserted into the surgical wound of a patient.

As seen in FIGS. 1 and 3, the bottom wall 32 of the liner is shown provided with a drainage emptying or discharge opening 50 which is closed by a removable or peelable seal member 52. The seal member 52 may be, for example, a plastic with a suitable non-drying adhesive if desired. The bottom wall 20 of the canister 12 is provided with an opening 54 in registration or in aligned relation with the discharge opening 50. If desired, the seal member 52 may be removed and drainage material allowed to flow out of the liner opening 50 and through the opening 54 in the canister while the liner is in the canister. The pleated liner 14 may be made of any suitable material such as a clear plastic or a combination of materials. The material and construction should be such that the sidewall 30 of the liner will not collapse under negative pressures expected during drainage collection procedures. Depending upon the expected negative pressures to be encountered, the liner 14 can be made, for example, of polypropylene or other plastic which will be vertically flexible enough to allow the liner to collapse vertically as in FIG. 2 and permit it to expand vertically as in FIG. 1, and without the sidewalls 30 collapsing laterally under negative pressure conditions while secured in the canister 12.

The suction outlet and drainage inlet ports 40 and 42 may be plastic tubes, for example, of moderately rigid polyvinyl chloride or the like. These ports or plastic tubes may be heat-welded or adhesively secured to the top wall portion 44 in fluid tight connection with the wall.

When it is desired to employ device 10 in collecting drainage fluid from the wound of a patient, a liner 14, such as in the collapsed condition in FIG. 2, is removed from its package. With the lid 22 removed from the container, the liner 14 may be inserted into the container 16 so that the lower wall 32 of the liner passes the liner holding abutment ring 38. The liner may then be manually expanded until the neck 36 extends past the upper open end of the container 16. The lid may then be threaded onto the neck 36 of the liner 14. The lid is then forced over the upper end of container 16 to secure the two in frictional engagement as in FIG. 1.

The vacuum and inlet ports 40 and 42 may be connected respectively to the tubes 46 and 48 to begin the drainage collecting procedure. With negative pressure within the chamber 45, wound drainage tends to flow into inlet port 42 and then into chamber 45 of the liner.

When it is desired to stop the drainage collection, lid 22, with the liner 14 attached, may be removed from the container 16, the lid unthreaded from the liner, and the liner stored or discarded. The tubes 46 and 48 may be discarded at the same time. If desired, some or most of the drainage material can be discharged through the opening 50 as previously mentioned.

When inserting a new liner 14, in some cases, depending on construction and size, a new liner may be first threaded onto the lid 22, and then the liner inserted into the container 16. The lower end of the liner can then be pulled down and past abutment 38 by grasping the bottom wall 32 through opening 54 in the canister.

In FIGS. 4 through 6, a modified embodiment is illustrated in which a relatively rigid plastic split canister 60 is shown which conveniently receives a pleated or accordion-like liner 62 (FIG. 5). Canister 60 is split or made in two parts 64 and 66 which are separate except that they are integrally connected together along a vertical, integral hinge indicated generally at 68 in FIG. 6. The canister parts 64 and 66 are shown as halves of the canister 60. When closed, the parts provide a generally cylindrical sidewall 70, a bottom wall 72, and a lid or upper end wall 74. A liner holding abutment ring 76 is shown interiorly of the canister and formed integrally adjacent the lower end of the canister for holding the lower end of liner 62 in the same manner as holding ring 38 in the embodiment of FIG. 1 holds liner 14.

The upper wall or lid 74 of the canister has a vertically extending collar 78 having an annular liner abutment holding ring 80 for holding the upper end portion of the liner 62 in place. As seen in FIG. 5, the liner 62 has an annular neck 82 which has an annular groove 84 which receives the holding ring 80 of canister 60. After the liner 62 is inserted into the canister with the canister open as in FIG. 4, the parts 64 and 66 are closed about the liner. The liner is inserted such that the abutment ring 76 will enter a pleat or overhang the bottom wall of the liner 62 and ring 80 will enter groove 84. In this way, the upper end portion or neck of the liner 62 is held in place by the cooperating ring 80 and groove 84, and the lower end of the liner is held in place by the engagement of ring 76 with a pleat or bottom wall of the liner.

Liner 62 is identical to liner 14 of FIG. 1 except that the neck 82 of liner 62 has a simple annular groove 84 instead of the threads of liner 14.

The canister 60 may be provided with any suitable means for maintaining it closed. For example, a button 88 on the exterior of sidewall 70 may be provided which cooperates with an integral flexible strap 90 having a buttonhole for receiving button 88. The bottom wall 72 of the canister may also be provided with an opening to allow discharge of the drainage collected from the bottom of liner 62 if desired.

Preferably, the sidewalls of the drainage collection liner are made of a suitable material pleated to form an accordion-like construction repeatably collapsible and extendable along the longitudinal axis of the liner substantially without undesirable change or deformation of the liner walls. In some cases, the sidewalls of the liner may be of plastic reinforced with other materials, such as other plastic fibers, to ensure that the sidewalls do not laterally collapse under the negative pressures expected to be encountered in use. Also, additional supporting means within the canister could be employed to ensure against lateral liner collapse during use.

As various changes could be made in the above construction without departing from the scope of the invention, it is intended that all matter contained in the above description and drawing shall be interpreted as illustrative and not in a limiting sense.

I claim:

1. A body fluid drainage collection device comprising a relatively rigid canister including a hollow container having a bottom wall and sidewalls connected to said bottom wall, and a lid connected to said sidewalls and having an opening therethrough, a flexible, collapsible drainage collection liner means removably insertable into said canister and having a lower portion with a bottom wall, sidewalls, and an upper portion with an upper wall integrally connected with said liner means bottom wall and sidewalls forming a drainage collection chamber, said liner means being collapsible to reduce the height thereof when free of said canister, suction outlet and drainage inlet conduits fixedly connected directly to said liner means upper wall and communicating with said chamber for communicating said chamber respectively with a source of vacuum and a source of body fluid drainage, both of said outlet and inlet conduits extending through said opening in said lid, and means connecting said liner means within said canister to maintain said liner means expanded during the application of vacuum to said outlet conduit including first connector means having securing abutment means on the walls of said opening of said lid, second connector means including a neck with abutment means on said upper wall of said liner means releaseably engageable with said abutment means on said walls of said opening of said first connector means to secure the upper portion of said liner to said lid, and holding means on said canister engageable with the lower portion of said liner means to circumferentially hold the lower portion in place, said sidewalls of said liner means being structured to prevent lateral collapse thereof without countervailing for the negative pressure on the inside of the liner means when said outlet is connected with a source of vacuum.

2. The device of claim 1 wherein said sidewalls of said liner means are in the form of bellows to resist lateral collapse thereof when said outlet is connected with a source of vacuum.

3. The device of claims 1 or 2 wherein said first connector means includes a first threaded connector on said lid, and said second connector means includes a second threaded connector on said upper wall of said liner means threadedly engageable with said first threaded connector.

4. The device of claim 3 wherein said first threaded connector includes an upwardly extending collar integral with said lid, and said second threaded connector includes an upwardly extending neck integral with said upper wall of said liner means threadedly engageable with said first threaded connector.

5. The device of claim 3 wherein said lid is removably connectable to said container sidewalls.

6. The device of claim 1 or 2 wherein said holding means includes an annular peripheral abutment on the interior of said container adjacent the lower end thereof engageable with the lower end portion of said liner means to hold it in place.

7. The device of claim 1 wherein said bottom wall of said liner includes means for providing a discharge opening therethrough for discharging drainage therefrom.

8. The device of claim 7 wherein said bottom wall of said canister includes an opening therethrough in registration with said means for providing said discharge opening.

9. The device of claim 1 or 2 wherein said liner is made of a material including plastic.

10. A body fluid drainage collection device comprising a relatively rigid canister including a hollow container having a bottom wall and sidewalls connected to said bottom wall, and a lid connected to said sidewalls, a flexible, collapsible drainage collection liner removably insertable into said canister and having a lower portion with a bottom wall, sidewalls, and an upper portion with an upper wall integrally connected with said liner bottom and sidewalls forming a drainage collection chamber, suction outlet and drainage inlet conduits connected directly to said liner and communicating with said chamber for communicating said chamber respectively with a source of vacuum and a source of body fluid drainage, and means connecting said liner within said canister to maintain said liner expanded during the application of vacuum to said outlet conduit including first connector means on said lid, second connector means on said upper wall of said liner releaseably engageable with said first connector means to secure the upper portion of said liner to said lid, and circumferential holding means on the interior walls of said canister engageable with the lower portion of said liner to hold the same in place, said lid including an upwardly extending integral collar, said liner being a substantially single-piece member, said upper wall of said liner including an upwardly extending integral neck receivable in said collar in concentric relation therewith, said neck having an upper wall portion, and said inlet and outlet conduits being connected to said upper wall portion in sealing connection therewith.

11. The device of claim 8 wherein said outlet and inlet conduits extend through said collar.

12. The device of claim 10 wherein said first and second connector means respectively include complementary threads on said collar and neck for threadedly connecting them together.

13. A body fluid drainage collection device comprising a relatively rigid canister including a hollow container having a bottom wall and sidewalls connected to said bottom wall, and a lid connected to said sidewalls, a flexible, collapsible drainage collection liner removably insertable into said canister and having a lower portion with a bottom wall, sidewalls, and an upper portion with an upper wall integrally connected with said liner bottom and sidewalls forming a drainage collection chamber, suction outlet and drainage inlet conduits connected directly to said liner and communicating with said chamber for communicating said chamber respectively with a source of vacuum and a source of body fluid drainage, and means connecting said liner within said canister to maintain said liner expanded during the application of vacuum to said outlet conduit including first connector means on said lid, second connector means on said upper wall of said liner releaseably engageable with said first connector means to secure the upper portion of said liner to said lid, and circumferential holding means on said canister interior walls engageable with the lower portion of said liner to hold the same in place, said first connector means including a collar on said lid with first peripherally extending abutment means thereon, said second connector means including a neck on said upper wall with second peripherally extending abutment means thereon engageable with said first abutment means to secure said upper portion of said liner relative to said canister.

14. The device of claim 1 or 13 wherein said canister is spilt into a pair of parts whereby said liner can be inserted between said parts, said parts being movable toward each other to effect engagement between said first and second abutment means.

15. The device of claim 14 wherein said canister is of plastic and further includes hinge means connecting said parts together for movement relative to each other.

16. The device of claim 15 wherein said canister is formed as an integral single-piece plastic member with said hinge means an integral portion of said member.

17. The device of claim 14 wherein said lid is integral with said sidewalls of said canister and said bottom wall, said sidewalls, and said lid of said canister are divided into two parts to permit said canister to be opened and closed.

18. The device of claim 14 wherein said sidewall of said liner is pleated to form a bellows-like configuration.

19. The apparatus of claim 10 or 13 wherein said liner is formed of a material including a plastic, said material being flexible and corrugated to permit collapse of said liner but rigid enough to prevent collapse of said liner while in said canister with suction applied to said suction outlet port at vacuum levels normally used for body fluid drainage.

* * * * *